United States Patent
Jiang et al.

(10) Patent No.: US 10,857,146 B2
(45) Date of Patent: Dec. 8, 2020

(54) METHOD FOR PREVENTING OR TREATING TUMOR DISEASES WITH A COMBINATION OF TYROSINE KINASE INHIBITOR AND CDK4/6 INHIBITOR

(71) Applicants: Jiangsu Hengrui Medicine Co., Ltd., Jiangsu (CN); Shanghai Hengrui Pharmaceutical Co., Ltd., Shanghai (CN)

(72) Inventors: Jiahua Jiang, Jiangsu (CN); Cheng Liao, Jiangsu (CN); Lianshan Zhang, Jiangsu (CN); Piaoyang Sun, Jiangsu (CN); Lin Shen, Jiangsu (CN); Jing Gao, Jiangsu (CN); Jifang Gong, Jiangsu (CN)

(73) Assignees: JIANGSU HENGRUI MEDICINE CO., LTD., Jiangsu (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 16/545,004

(22) Filed: Aug. 20, 2019

(65) Prior Publication Data

US 2020/0061049 A1    Feb. 27, 2020

(30) Foreign Application Priority Data

Aug. 21, 2018  (CN) .......................... 2018 1 0955518
Jun. 20, 2019  (CN) .......................... 2019 1 0537015

(51) Int. Cl.
| | | |
|---|---|---|
| *A61K 31/4709* | (2006.01) | |
| *A61P 35/00* | (2006.01) | |
| *A61K 45/06* | (2006.01) | |

(52) U.S. Cl.
CPC .......... *A61K 31/4709* (2013.01); *A61P 35/00* (2018.01); *A61K 45/06* (2013.01)

(58) Field of Classification Search
CPC .......................... A61K 31/4709; A61P 35/00
See application file for complete search history.

(56) References Cited

U.S. PATENT DOCUMENTS 8,901,140 B2 * 12/2014 Tang ................... C07D 401/12
                                                514/266.21

FOREIGN PATENT DOCUMENTS

| CN | 102933574 A | 2/2013 |
| WO | 2011029265 A1 | 3/2011 |
| WO | 2014183520 A1 | 11/2014 |
| WO | 2016124067 A1 | 8/2016 |

OTHER PUBLICATIONS

Barvian et al. (CN 101001857, 2007, English Description Translation.*
Goel et al, "Overcoming Therapeutic Resistance in HER2-Positive Breast Cancers with CDK4/6 Inhibitors," Cancer Cell, vol. 29, pp. 255-269 (Mar. 14, 2016).

* cited by examiner

*Primary Examiner* — Samira J Jean-Louis
(74) *Attorney, Agent, or Firm* — Ice Miller LLP

(57) ABSTRACT

A method for preventing or treating tumor diseases with a combination of a tyrosine kinase inhibitor and a CDK4/6 inhibitor is provided. In particular, a method for preventing or treating tumor diseases, including administering to a patient a tyrosine kinase inhibitor of a compound of formula (I), or a complex, a pharmaceutically acceptable salt or a stereoisomer thereof and a CDK4/6 inhibitor is provided.

12 Claims, 3 Drawing Sheets

Days after administration (day)

METHOD FOR PREVENTING OR TREATING TUMOR DISEASES WITH A COMBINATION OF TYROSINE KINASE INHIBITOR AND CDK4/6 INHIBITOR

This application claims priority under 35 U.S.C. § 119(b) to Chinese Application No. 201910537015.4, filed Jun. 20, 2019 and Chinese Application No. 201810955518.9, filed Aug. 21, 2018, the disclosures of which are incorporated herein by reference in their entirety.

FIELD OF THE INVENTION

The present application belongs to the field of medicine, and relates to a method for preventing or treating tumor diseases with a combination of a tyrosine kinase inhibitor and a CDK4/6 inhibitor.

BACKGROUND OF THE INVENTION

Malignant tumor is a major disease that endangers people's lives and health. In recent years, with the rapid development of tumor biology and related disciplines, specific anti-tumor drugs targeting abnormal signaling systems in tumor cells are the focus of new drug development. At the same time, a combination of various anti-tumor drugs for treating tumor diseases has also become a scientific research hotspot.

Receptor tyrosine kinase is a class of transmembrane proteins involved in signal transduction. It is expressed in a variety of cells, and regulates the growth, differentiation and neovascularization of cells. Studies have shown that more than 50% of the proto-oncogene and oncogene products have a tyrosine kinase activity, the abnormal expression of which causes tumorigenesis, and is also closely related to tumor invasion and metastasis, tumor neovascularization, and chemotherapy resistance of tumors. A number of tyrosine kinase inhibitors, such as Lapatinib and Neratinib, have been disclosed at present. WO2011029265 discloses an effective tyrosine kinase inhibitor and a preparation method thereof, and its structure is as shown in formula I:

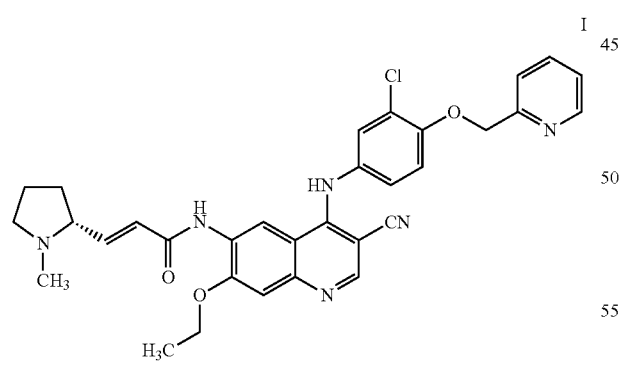

I

This compound has a significant pharmacodynamic advantage. CN102933574A discloses a dimaleate of the compound, which has an improved physicochemical property, pharmacokinetic property and bioavailability.

Moreover, a number of studies have shown that tumors are related to cell cycle abnormality. Most of the tumors have a number of mutations in mitotic signaling proteins/defects in anti-mitotic signaling proteins, genome instability (GIN) and chromosome complement instability (CIN). These three basic cell cycle defects are all induced directly or indirectly by the uncontrolled cyclin-dependent kinases (CDKs). Cyclin B/CDK1, Cyclin A/CDK2, Cyclin E/CDK2, Cyclin D/CDK4, Cyclin D/CDK6, and other heterodimers (including CDK3 and CDK7) are important regulators of cell cycle progression. A number of CDK inhibitors have been disclosed at present, wherein the CDK4/6 inhibitor includes abemaciclib, ribociclib, palbociclib and the like. WO2014183520 provides an effective CDK4/6 inhibitor, and its structure is as shown in formula II:

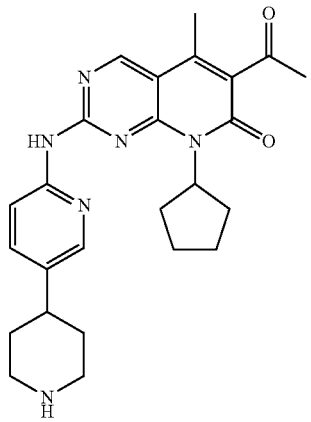

II

WO2016124067 discloses an isethionate of the above new CDK4/6 inhibitor.

The prior art discloses a number of regimens for treating tumor diseases with a combination of tyrosine kinase inhibitor and CDK4/6 inhibitor. Shom Goel et al (Cancer Cell 29, 255-269) report the treatment of lapatinib-resistant HER-2 positive breast cancer cells with a combination of lapatinib and abemaciclib. The result shows that lapatinib and abemaciclib can effectively inhibit the viability of breast cancer cells synergistically upon combined treatment.

The present application provides a new method for preventing or treating tumor diseases with a combination of a new tyrosine kinase inhibitor and CDK4/6 inhibitor, which shows a good anti-tumor effect.

SUMMARY OF THE INVENTION

The present application provides a method for preventing or treating tumor diseases, comprising administration of a tyrosine kinase inhibitor and a CDK4/6 inhibitor to a patient, wherein the tyrosine kinase inhibitor is a compound of formula (I), or a complex, a pharmaceutically acceptable salt or a stereoisomer thereof,

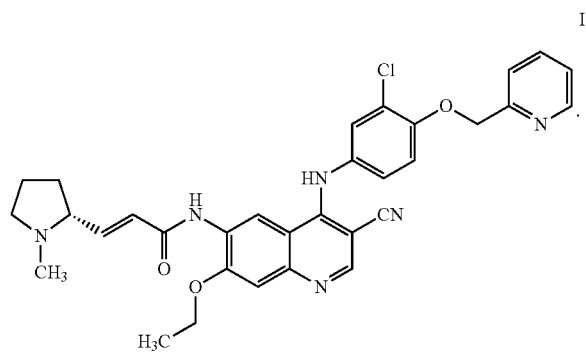 [SMILES: CCOc1cc2ncc(C#N)c(Nc3ccc(OCc4ccccn4)c(Cl)c3)c2cc1NC(=O)/C=C/[C@H]1CCCN1C]

I

In certain embodiments, the CDK4/6 inhibitor can be abemaciclib, ribociclib, palbociclib, alvocidib, trilaciclib, voruciclib, AT-7519, G1T-38, FLX-925, INOC-005, G1T28-1, BPI-1178, gossypin, G1T30-1, GZ-38-1, P-276-00, staurosporine, R-547, PAN-1215, PD-0183812, AG-024322, NSC-625987, CGP-82996, PD-171851 or a compound of formula (II), preferably abemaciclib, ribociclib, palbociclib, alvocidib or a compound of formula (II), and more preferably a compound of formula (II), or a complex or a pharmaceutically acceptable salt thereof,

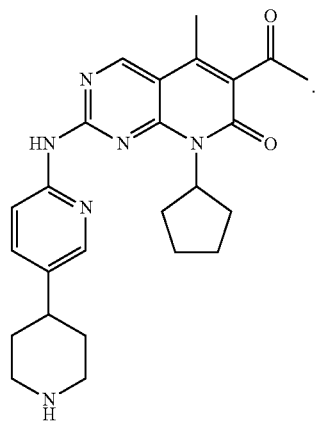

II

In certain embodiments, the tumor disease can be a breast tumor, ovarian cancer, prostate cancer, melanoma, brain tumor, esophageal cancer, gastric cancer, liver cancer, pancreatic cancer, colorectal cancer, lung cancer, kidney cancer, skin cancer, glioblastoma, neuroblastoma, sarcoma, liposarcoma, osteochondroma, osteoma, osteosarcoma, seminoma, testicular tumor, uterine cancer, head and neck tumor, multiple myeloma, malignant lymphoma, polycythemia vera, leukemia, thyroid tumor, ureter tumor, bladder tumor, gallbladder cancer, cholangiocarcinoma or chorionic epithelioma.

In certain embodiments, the tumor disease is selected from HER2 positive and HER2 mutant tumors.

In certain embodiments, the tumor disease is selected from HER2 positive and HER2 mutant breast cancer or gastric cancer.

In certain embodiments, the gastric cancer comprises gastroesophageal junction cancer.

In certain embodiments, the gastric cancer is HER2 inhibitor-resistant gastric cancer. In certain embodiments, the HER2 inhibitor is one or more HER2 inhibitors selected from trastuzumab, pertuzumab, lapatinib, alfatinib, canertinib, neratinib and the compound of formula (I), and preferably the compound of formula (I).

In certain embodiments, the breast tumor is selected from nipple tumor, male breast tumor, breast malignant lymphoma, fibroepithelial tumor, epithelial-myoepithelium tumor, intraductal carcinoma, lobular carcinoma in situ, papillary eczema-like breast cancer, early invasive ductal carcinoma, early invasive lobular carcinoma, papillary carcinoma, medullary carcinoma, tubular carcinoma, adenoid cystic carcinoma, mucinous adenocarcinoma, apocrine adenoid carcinoma, squamous cell carcinoma, invasive lobular carcinoma, invasive ductal carcinoma and scirrhous carcinoma.

In a preferred embodiment of the present application, the weight ratio of the compound of formula (I), or a complex, a pharmaceutically acceptable salt or a stereoisomer thereof to the CDK4/6 inhibitor is in the range of 0.01:1 to 100:1, and preferably 1:0.1, 1:0.125, 1:0.14, 1:0.15, 1:0.175, 1:0.1875, 1:0.2, 1:0.25, 1:0.28, 1:0.3, 1:0.35, 1:0.4, 1:0.5, 1:0.7, 1:0.75, 1:1, 1:1.25, 1:1.75, 1:2, 1:2.5, 1:3.5, 1:4, 1:5, 1:8, 1:10, 1:15, 2:15, 1:20, 1:25, 3:1, 3:2, 6:1, 6:5, 6:7, 8:5, 8:7, 12:1, 15:7, 16:3, 16:5, 16:7, 16:15, 16:25, 16:35, 24:5, 24:7, or 60:7.

In another preferred embodiment of the present application, the dose of the compound of formula (I), or a complex, a pharmaceutically acceptable salt or a stereoisomer thereof is in the range of 100 to 1000 mg; and the dose of the CDK4/6 inhibitor is in the range of 1 to 1000 mg.

In certain embodiments, the dose of the compound of formula (I), or a complex, a pharmaceutically acceptable salt or a stereoisomer thereof is selected from 100 mg, 125 mg, 150 mg, 175 mg, 200 mg, 250 mg, 300 mg, 350 mg, 400 mg, 450 mg, 500 mg, 600 mg, 700 mg, 750 mg, 800 mg, 900 mg and 1000 mg.

The dose of the CDK4/6 inhibitor of the present application is selected from 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 100 mg, 125 mg, 150 mg, 175 mg, 200 mg, 250 mg, 300 mg, 350 mg, 400 mg, 450 mg, 500 mg, 600 mg, 700 mg, 750 mg, 800 mg, 900 mg and 1000 mg.

The pharmaceutically acceptable salt of the drug of the present application may be hydrochloride, phosphate, hydrophosphate, sulfate, hydrosulfate, sulfite, acetate, oxalate, malonate, valerate, glutamate, oleate, palmitate, stearate, laurate, borate, p-toluenesulfonate, methanesulfonate, isethionate, maleate, malate, tartrate, benzoate, pamoate, salicylate, vanillate, mandelate, succinate, gluconate, lactobionate, and lauryl sulfonate and the like.

In certain embodiments, the pharmaceutically acceptable salt of the compound of formula (I) is maleate, and preferably dimaleate.

In certain embodiments, the pharmaceutically acceptable salt of the compound of formula (II) is isethionate.

The way of the combination administration of the present publication is simultaneous administration, co-administration after separate formulation or sequential administration after separate formulation.

The route of the combination administration of the present application is selected from oral administration, parenteral administration and transdermal administration, and the parenteral administration includes, but is not limited to, intravenous injection, subcutaneous injection and intramuscular injection.

The present publication further relates to a method for preventing or treating tumor diseases, comprising administration of a compound of formula (I), or a complex, a pharmaceutically acceptable salt or a stereoisomer thereof and a CDK4/6 inhibitor to a patient, wherein the compound of formula (I), or a complex, a pharmaceutically acceptable salt or a stereoisomer thereof can be administrated once a day, twice a day, three times a day, once a week, once every two weeks, once every three weeks or once a month, and the CDK4/6 inhibitor can be administrated once a day, twice a day, three times a day, once a week, once every two weeks, once every three weeks or once a month.

In certain embodiments, the compound of formula (I), or a complex, a pharmaceutically acceptable salt or a stereoisomer thereof is administrated once a day, and the CDK4/6 inhibitor is administrated once a day.

In certain embodiments, the administration period is 21 days, the compound of formula (I), or a complex, a pharmaceutically acceptable salt or a stereoisomer thereof is administrated once a day continuously, and the CDK4/6 inhibitor is administrated once a day continuously.

In certain embodiments, the administration period is 28 days, the compound of formula (I), or a complex, a pharmaceutically acceptable salt or a stereoisomer thereof is administrated once a day continuously for four weeks, and the CDK4/6 inhibitor is administrated once a day continuously for three weeks followed by one week of withdrawal.

In certain embodiments, the administration period is 28 days, the compound of formula (I), or a complex, a pharmaceutically acceptable salt or a stereoisomer thereof is administrated once a day continuously for four weeks with a dose of 400 mg or 320 mg per day, and the CDK4/6 inhibitor is administrated once a day continuously for three weeks with a dose of 100 mg, 125 mg, 150 mg or 175 mg per day followed by one week of withdrawal.

In an embodiment of the present invention, the combination administration also optionally comprises other components including, but not limited to, other anti-tumor drugs and the like.

The present application also provides a method for preventing or treating tumor diseases, comprising administration of a compound of formula (I), or a complex, a pharmaceutically acceptable salt or a stereoisomer thereof and a CDK4/6 inhibitor to a patient, wherein the CDK4/6 inhibitor is a compound of formula (II), or a complex or a pharmaceutically acceptable salt thereof.

The present publication also provides a method for treating tumor diseases, comprising administration of a compound of formula (I), or a complex, a pharmaceutically acceptable salt or a stereoisomer thereof and a CDK4/6 inhibitor of the present application.

The present application also relates to a pharmaceutical composition comprising a compound of formula (I), or a complex, a pharmaceutically acceptable salt or a stereoisomer thereof, and a CDK4/6 inhibitor, as well as one or more pharmaceutically acceptable carriers, excipients or diluents. The pharmaceutical composition can be formulated into any pharmaceutically acceptable formulations. For example, the pharmaceutical composition can be formulated into a tablet, capsule, pill, granule, solution, suspension, syrup, injection (including injection solution, sterile powder for injection and concentrated solution for injection), suppository, inhalant or spray.

The pharmaceutical composition comprising a compound of formula (I), or a complex, a pharmaceutically acceptable salt or a stereoisomer thereof and a CDK4/6 inhibitor according to the present invention can be administrated separately, or in combination with one or more other therapeutic agents.

Each of the components to be combined (such as the compound of formula (I), or a complex, a pharmaceutically acceptable salt or a stereoisomer thereof and the CDK4/6 inhibitor, or the compound of formula (I), or a complex, a pharmaceutically acceptable salt or a stereoisomer thereof, and the CDK4/6 inhibitor and other drugs) can be administrated simultaneously or sequentially. In addition, each of the components to be combined can also be administrated in combination in the same formulation or in separate formulations.

The present application also provides a drug package comprising the pharmaceutical composition of a tyrosine kinase inhibitor and a CDK4/6 inhibitor of the present invention, wherein the tyrosine kinase inhibitor is a compound of formula (I), or a complex, a pharmaceutically acceptable salt or a stereoisomer thereof.

The term "combination administration" herein refers to an administration way, which means that at least one dose of the compound of formula (I) and at least one dose of the CDK4/6 inhibitor are administrated within a certain period of time, wherein the drugs administrated all show pharmacological effects. The period of time can be one administration period, preferably four weeks, three weeks, two weeks, one week or 24 hours, and more preferably 12 hours. The compound of formula (I) and the CDK4/6 inhibitor can be administrated simultaneously or sequentially. The period of time comprises the treatment, wherein the compound of formula (I) and CDK4/6 inhibitor are administrated in a same administration route or different administration routes. The combination administration way of the present application is selected from simultaneous administration, co-administration after separate formulation and sequential administration after separate formulation.

In the present application, the compound of formula (I), or a complex, pharmaceutically acceptable salt or a stereoisomer thereof and the CDK4/6 inhibitor are administrated in combination, thereby obtaining an increased anti-tumor activity and improved therapeutic effect of tumor diseases.

DESCRIPTION OF THE DRAWINGS

FIG. 4A shows the tumor growth curve in the drug-resistant PDX model after administration of single drug or combination administration, and FIG. 4B shows the change in the expression of several key molecules of the cell cycle determined by Western blot method before and after drug administration.

DETAILED DESCRIPTION OF THE INVENTION

Figure 1:
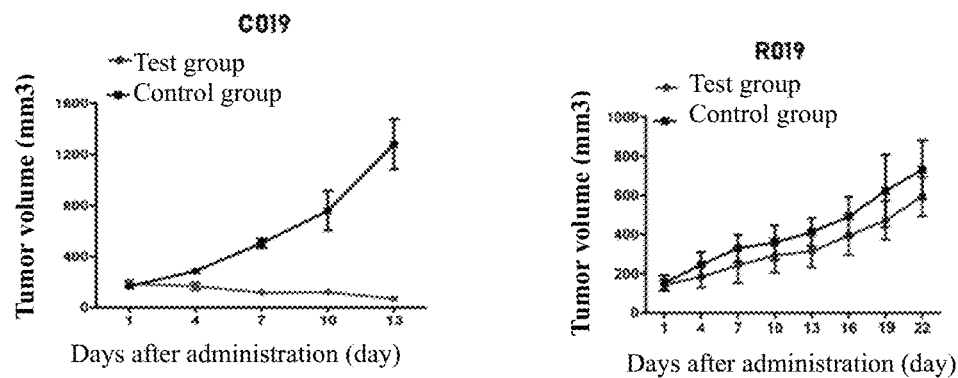
FIG. 1 shows the identification of the PDX model of secondary HER2 inhibitor-resistant gastric cancer.

Example 1: Study on the Efficacy of Combination Administration and Separate Administration of the Compound of Formula (I) and the Compound of Formula (II) on Breast Cancer PDX (ER−, HER2+) BALB/c Nude Mice 1. Test Drug Name: the dimaleate of the compound of formula (I) prepared according to the method disclosed in CN102933574A; the isethionate of the compound of formula (II) prepared according to the method disclosed in WO2016124067.

Formulating method: the dimaleate of the compound of formula (I) was formulated with distilled water; the isethionate of the compound of formula (II) was formulated with a solution of 0.05 M citric acid/0.5% CMC-Na/1% Tween 80 (w/v) in deionized water.

2. Test Animals

BALB/c nude mice (6-8 weeks old, female) were purchased from Beijing Vital River Laboratory Animal Technology Co., Ltd., with Certificate No.: SCXK (HU) 2015-0022. Feeding environment: SPF level.

Feeding environment: controlled temperature: 20 to 26° C.; controlled relative humidity: 40% to 70%; lighting: automatic lighting, light and dark were alternated every 12 hours.

3. Test Procedures

The breast tumor (invasive ductal carcinoma of grade III, derived from epithelial cells) from the patient was cut into pieces (15-30 mm$^3$) in the 1640 culture medium, and then inoculated subcutaneously into the nude mice. After the tumor grew to 600-700 mm$^3$, passage was carried out on the nude mice. When the eighth generation (P8) of tumor grew to 600-700 mm$^3$, the tumor was cut into pieces (15-30 mm$^3$) in the 1640 culture medium for subcutaneous inoculation to the test nude mice. After the tumor grew to 200-250 mm$^3$, the animals were randomly grouped and administrated with drugs. The test groups were divided into control group, group of the dimaleate of the compound of formula (I) alone (administration dose: 5 mg/kg, 10 mg/kg), group of the isethionate of the compound of formula (II) alone (administration dose: 150 mg/kg), group of the combination of the dimaleate of the compound of formula (I) and the isethionate of the compound of formula (II) (administration dose: 5 mg/kg+150 mg/kg, 10 mg/kg+150 mg/kg), with six animals in each group. The administration volume of each group was 10 ml/kg. The drugs were administrated intragastrically once a day for three weeks. The tumor volume and mouse weight were measured two to three times a week and recorded. The tumor volume (V) was calculated by the following formula:

$$V=1/2 \times a \times b2,$$

wherein a and b represent tumor length and width respectively.

$$T/C(\%)=(T-T0)/(C-C0) \times 100\%,$$

wherein T and C represent the tumor volume at the end of the test in the therapy group and control group, respectively; T0, C0 represent the tumor volume at the beginning of the test in the therapy group and control group, respectively.

Example 2: Study on the Efficacy of Combination Administration and Separate Administration of the Compound of Formula (I) and the Compound of Formula (II) on HER2 Inhibitor-Resistant Gastric Cancer PDX Mice HER2 inhibitor-sensitive PDX model and HER2 inhibitor-resistant PDX model were constructed as follows (the compound of formula (I) is a HER2 inhibitor):

A large-scale patient-derived tumor xenograft (PDX) model was constructed with a small amount of advanced gastric cancer tissue obtained by real-time endoscopic biopsy, thereby establishing a PDX tissue library. The PDX tissue was taken from the PDX tissue library, revived and inoculated subcutaneously into the mice. When the tumor volume reached 150-200 mm$^3$ (it took about one month), the administration of the compound of formula (I) was carried out and lasted for three months (intragastrically, once a day, in a single dose of 20 mg/kg), and the tumor showed resistance to 20 mg/kg of the compound of formula (I). The tumor tissue was separated, and re-inoculated into new mice. When the tumor volume reached 150-200 mm$^3$ (it took about one month), the administration of the compound of formula (I) was carried out and lasted for three months (intragastrically, once a day, in a single dose of 40 mg/kg), and the tumor showed complete resistance to 40 mg/kg of the compound of formula (I). C019 represents the mice one month after subcutaneous inoculation of the revived PDX tissue, S019 represents the mice two weeks after the administration of the compound of formula (I) at a single dose of 20 mg/kg, and R019 represents the mice three months after the administration of the compound of formula (I) in a single dose of 40 mg/kg.

Protocol of the drug resistance test: the inhibitor group was administrated with the compound of formula (I) (intragastrically, once a day, in a single dose of 40 mg/kg), and the control group was administrated with an equal volume of normal saline. The tumor volume was measured every three days. The result of drug sensitivity of C019 and R019 models is shown in FIG. 1 (average value of five mice). C019 is highly sensitive to the compound of formula (I), and the tumor inhibition rate of the compound of formula (I) is >100%. R019 shows high resistance to the compound of formula (I).

Figure 2:
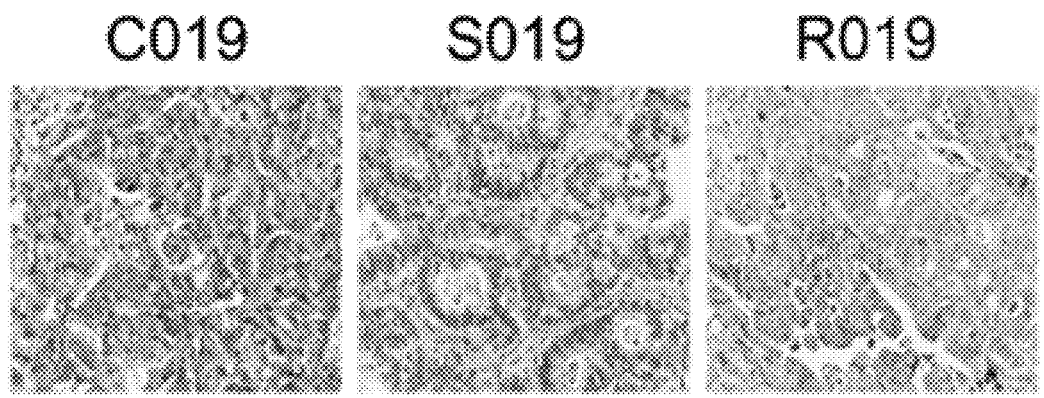
FIG. 2 shows the identification of the pathomorphological consistency of PDX tissue before and after drug resistance.

The PDX tissues of C019, S019 and R019 were subjected to hematoxylin and eosin (HE) staining, and the results are shown in FIG. 2. The pathomorphology of PDX tissues remained consistent after prolonged drug induction.

Figure 3:
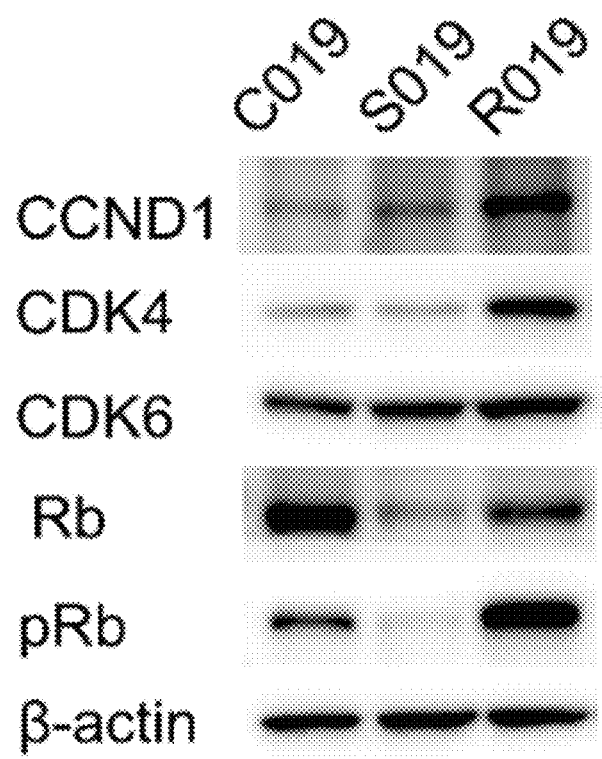
FIG. 3 shows the change in the expression of several key molecules of the cell cycle in the tissue determined by Western blot method before and after drug resistance.

The PDX tissues (the PDX tissue of C019, the PDX tissue of S019 and the PDX tissue of R019) before and after drug resistance were subjected to a transcriptome sequencing, and the sequencing results were subjected to a signaling pathway enrichment analysis. It is found that the abnormal regulation enrichment of the cell cycle in the tissue after drug resistance is more significant compared with the tissue before drug resistance. The tissues before and after drug resistance were verified with Western blot. It was found that the expression levels of key molecules involved in cell cycle regulation (cyclin D1, CDK4/6, pRb and the like) were significantly up-regulated in the tissue after drug resistance (FIG. 3). In particular, the phosphorylation of Rb, a downstream effector molecule of CDK4/6 and cyclin D1, was significantly increased. Therefore, the inventors speculate that the abnormality of cyclin D1-CDK4/6 pathway may be involved in the HER2-targeted therapy resistance of gastric cancer, and the combination with a CDK4/6 inhibitor may become a therapeutic strategy after drug resistance. This hypothesis was validated in the drug-resistant PDX model.

Protocol of Combination Administration:

The administrations to the HER2 inhibitor-resistant PDX models (R019 mice, 5 mice per group) were carried out according to the following groups:

Group I (control group): intragastrical (oral) administration of normal saline with a single volume of 100 μl per mouse, once a day, for three weeks;

Group II (HER2 inhibitor group): intragastrical (oral) administration of the compound of formula (I) with a single volume of 100 μl per mouse and a single dose of "40 mg/kg of the compound of formula (I)", once a day, for three weeks;

Group III (CDK4/6 inhibitor group): intragastrical (oral) administration of the compound of formula (II) with a single volume of 100 μl per mouse and a single dose of "100 mg/kg of the compound of formula (II)", once a day, for three weeks;

Group IV (combination of CDK4/6 inhibitor and HER2 inhibitor group): intragastrical (oral) administration of the compound of formula (I) and the compound of formula (II) with a single volume of 100 μl per mouse and a single dose of "40 mg/kg of the compound of formula (I)" and "100 mg/kg of the compound of formula (II)", once a day, for three weeks.

Figure 4A:
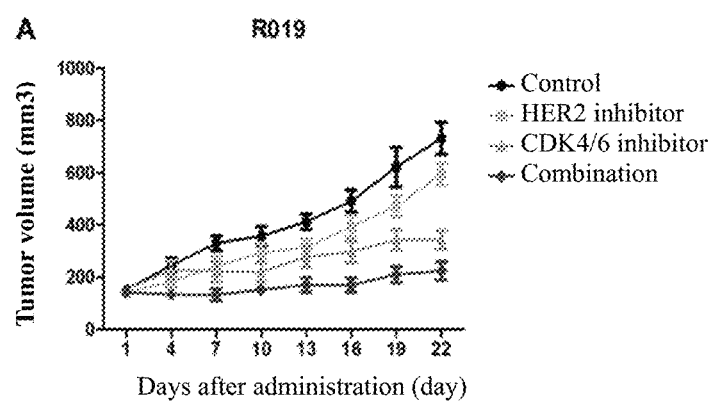
FIGS. 4A and 4B show tumor growth and change in the expression of molecules of the cell cycle in a drug-resistant PDX model.

The tumor volume was measured every three days. The results are shown in FIG. 4A. The combination of a CDK4/6 inhibitor and a HER2 inhibitor shows a significant synergistic anti-tumor effect.

Figure 4B:
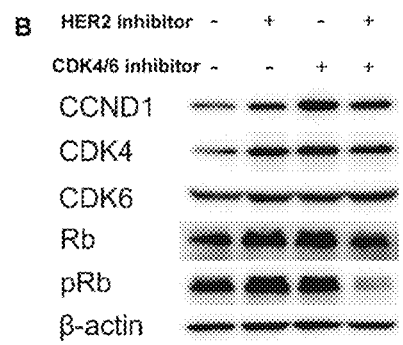

After combination administration, the expression of key molecules involved in the cell cycle (cyclin D1, CDK4/6, pRb and the like, especially pRb) in tissues was down-regulated and cell division was arrested at G1 phase. The combination administration thus shows an anti-tumor effect (FIG. 4B).

Example 3: Study on the Combination Administration of the Compound of Formula (I) and the Compound of Formula (II) in Treating HER2 Positive Advanced Gastric Cancer 1. Test Drug Tablets of the dimaleate of the compound of formula (I), specification: 40 mg, 60 mg, 200 mg, 160 mg and 80 mg.

Tablets of the isethionate of the compound of formula (II), specification: 125 mg and 25 mg.

2. Enrolled Subjects (1) Age: 18-75 years old;
(2) ECOG score: level 0-1;
(3) Patients suffered from a pathologically confirmed HER2 positive gastric cancer (including gastroesophageal junction cancer) with a clinical stage of stage III or IV ("HER2 positive" means that it is confirmed positive by fluorescence in situ hybridization (FISH) and the immuno-histochemical staining is 2+, or the immunohistochemical staining is 3+);
(4) The patients have previously received systematic treatment for metastatic disease, and have progression of disease.

3. Administration Method

Qualified subjects were screened, and administrated with the compound of formula (I) and the compound of formula (II). The administration period was 21 or 28 days. The compound of formula (I) was orally administered once a day with an administration dose of 400 mg or 320 mg per day. The compound of formula (II) was orally administered once a day with an administration dose of 100 mg, 125 mg, 150 mg or 175 mg per day. The administration was continuous until progression of disease, intolerance to toxicity or the patient refused to continue treatment. The pathological remission of the patients was evaluated.

4. Test Results

A total of three treated subjects were evaluated. The administration period was 28 days. 400 mg of the compound of formula (I) was orally administered once a day continuously for four weeks. 100 mg of the compound of formula (II) was orally administered once a day continuously for three weeks followed by one week of withdrawal.

Patient A received a reduction of lesions after two periods of treatment, and was evaluated as stable disease (SD). The tumor markers CEA, CA199 and CA72.4 were reduced from 121.4 ng/ml, 60 U/ml and 5.4 U/ml before the treatment to 15.8 ng/ml, 45.3 U/ml and 4.1 U/ml after the treatment, respectively. Patient A benefited significantly from the treatment.

Patient B received a very significant reduction of lesions after two periods of treatment, and was evaluated as partial response (PR). The tumor markers CEA, CA199 and CA72.4 were reduced from 122.2 ng/ml, 1871 U/ml and 23.54 U/ml before treatment to 26.97 ng/ml, 86.1 U/ml and 7.92 U/ml, respectively. Patient B received a significant reduction of lesions, and benefited significantly from the treatment.

Patient C received a very significant reduction of lesions after two periods of treatment (the tumor was reduced by about 20%), and was evaluated as SD. The tumor markers CEA, CA199 and CA72.4 were reduced from 5.49 ng/ml, 250.1 U/ml and 78.46 U/ml before treatment to 1.92 ng/ml, 14.32 U/ml and 12.74 U/ml, respectively. Patient C received a significant reduction of lesions, and benefited significantly from the treatment.

What is claimed is:

1. A method for treating gastric cancer, comprising administration of a compound of formula (I), or a pharmaceutically acceptable salt or a stereoisomer thereof and a CDK4/6 inhibitor to a patient:

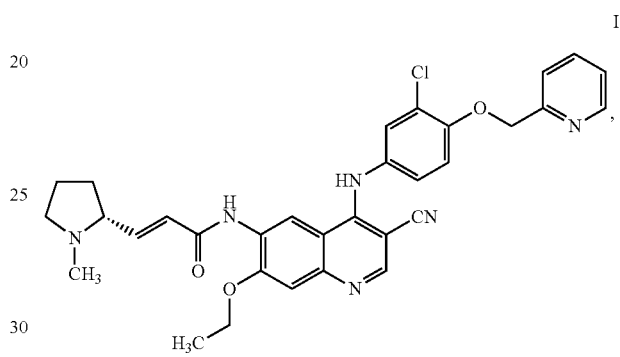

wherein the CDK4/6 inhibitor is a compound of formula (II), or a pharmaceutical acceptable salt thereof:

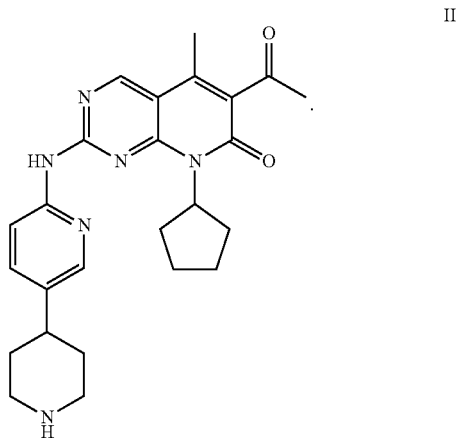 [SMILES: CC(=O)c1c(C)c2cnc(Nc3ccc(C4CCNCC4)cn3)nc2n(C2CCCC2)c1=O]

2. The method according to claim 1, wherein the gastric cancer is selected from a HER2 positive and a HER2 mutant gastric cancer.

3. The method according to claim 1, wherein the gastric cancer is selected from a HER2 inhibitor-resistant gastric cancer; and the HER2 inhibitor is one or more HER2 inhibitors selected from trastuzumab, pertuzumab, lapatinib, alfatinib, canertinib, neratinib and the compound of formula (I), or a pharmaceutically acceptable salt or a stereoisomer thereof.

4. The method according to claim 1, wherein the pharmaceutically acceptable salt of the compound of formula (I) is maleate.

5. The method according to claim 1, wherein the pharmaceutically acceptable salt of the compound of formula (II) is isethionate.

6. The method according to claim 1, wherein a weight ratio of the compound of formula (I), or a pharmaceutically acceptable salt or a stereoisomer thereof to the CDK4/6 inhibitor is in a range of 0.01:1 to 100:1.

7. The method according to claim 1, wherein a dose of the compound of formula (I), or a pharmaceutically acceptable salt or a stereoisomer thereof is in a range of 100 mg to 1000 mg.

8. The method according to claim 1, wherein a dose of the CDK4/6 inhibitor is in a range of 1 mg to 1000 mg.

9. A pharmaceutical composition comprising a compound of formula (I), or a pharmaceutically acceptable salt or a stereoisomer thereof and a CDK4/6 inhibitor, and one or more pharmaceutically acceptable excipients, diluents or carriers:

wherein the CDK4/6 inhibitor is a compound of formula (II), or a pharmaceutical acceptable salt thereof:

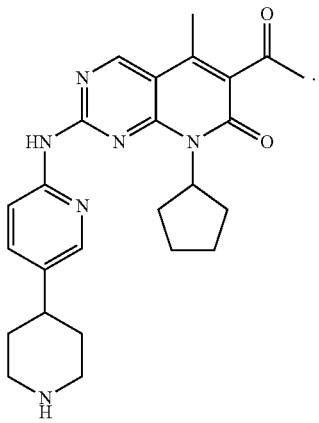

10. The method according to claim 4, wherein the pharmaceutically acceptable salt of the compound of formula (I) is dimaleate.

11. The method according to claim 6, wherein the weight ratio of the compound of formula (I), or a pharmaceutically acceptable salt or a stereoisomer thereof to the CDK4/6 inhibitor is 1:0.1, 1:0.125, 1:0.14, 1:0.15, 1:0.175, 1:0.1875, 1:0.2, 1:0.25, 1:0.28, 1:0.3, 1:0.35, 1:0.4, 1:0.5, 1:0.7, 1:0.75, 1:1, 1:1.25, 1:1.75, 1:2, 1:2.5, 1:3.5, 1:4, 1:5, 1:8, 1:10, 1:15, 2:15, 1:20, 1:25, 3:1, 3:2, 6:1, 6:5, 6:7, 8:5, 8:7, 12:1, 15:7, 16:3, 16:5, 16:7, 16:15, 16:25, 16:35, 24:5, 24:7, or 60:7.

12. The pharmaceutical composition according to claim 9, wherein the pharmaceutically acceptable salt of the compound of formula (I) is maleate.

* * * * *